US008211485B2

(12) United States Patent
Ahmedna et al.

(10) Patent No.: US 8,211,485 B2
(45) Date of Patent: Jul. 3, 2012

(54) PROCESS FOR PREPARING HYPOALLERGENIC AND NON-ALLERGENIC PEANUTS (*ARACHIS HYPOGAEA*) UTILIZING AN ENDOPEPTIDASE

(75) Inventors: Mohamed Ahmedna, Greensboro, NC (US); Jianmei Yu, Greensboro, NC (US); Ipek Goktepe, Greensboro, NC (US)

(73) Assignee: North Carolina A&T State University, Greensboro, NC (US)

( * ) Notice: Subject to any disclaimer, the term of this patent is extended or adjusted under 35 U.S.C. 154(b) by 48 days.

(21) Appl. No.: 11/758,823

(22) Filed: Jun. 6, 2007

(65) Prior Publication Data

US 2008/0305211 A1 Dec. 11, 2008

(51) Int. Cl.
*A23L 1/36* (2006.01)
(52) U.S. Cl. .......... 426/44; 426/615; 426/629; 426/632; 435/219
(58) Field of Classification Search .......... None
See application file for complete search history.

(56) References Cited

U.S. PATENT DOCUMENTS

| 2,294,682 A |   | 9/1942 | Moss |
|---|---|---|---|
| 3,829,589 A | * | 8/1974 | Matsunaga .................. 426/427 |
| 4,078,092 A |   | 3/1978 | Nishiyama |
| 4,443,540 A |   | 4/1984 | Chervan et al. |
| 4,627,983 A | * | 12/1986 | Scharf et al. .................. 426/7 |
| 5,039,532 A |   | 8/1991 | Jost et al. |
| 5,266,473 A |   | 11/1993 | Nielsen |
| 5,480,660 A |   | 1/1996 | Ikezawa et al. |
| 5,753,296 A |   | 5/1998 | Girsh |
| 5,891,493 A | * | 4/1999 | Santillo, Jr. .................. 426/44 |
| 6,197,356 B1 |   | 3/2001 | Girsh |
| 6,284,292 B1 |   | 9/2001 | Nielsen et al. |
| 6,486,311 B1 |   | 11/2002 | Burks et al. |
| 2003/0203089 A1 | * | 10/2003 | Meibach et al. .................. 426/431 |
| 2004/0058051 A1 |   | 3/2004 | Yunusov et al. |
| 2004/0265234 A1 |   | 12/2004 | Morimatsu et al. |
| 2005/0015826 A1 |   | 1/2005 | Kinney et al. |
| 2005/0114924 A1 |   | 5/2005 | Dodo et al. |

OTHER PUBLICATIONS

E.W. Lusas 1979 (J. Am. Oil Chemists' Soc. vol. 56 p. 425-430).*
Akintunde et al. Journal of Food Technology in Africa Apr.-Jun. 2002 vol. 7 No. 2 p. 55-58.*

(Continued)

*Primary Examiner* — Humera Sheikh
*Assistant Examiner* — Felicia King
(74) *Attorney, Agent, or Firm* — Smith Moore Leatherwood LLP; Clara R. Cottrell

(57) ABSTRACT

The present invention relates to the use of a solution containing at least one endopeptidase to substantially reduce or completely eliminate allergenic proteins contained in the peanut (*Arachis hypogea*). In particular, the direct application of a solution containing at least one endopeptidase to either raw, blanched, or roasted peanuts or peanut products or derivates, has been shown to substantially reduce or completely eliminate the activity of allergenic proteins. The treated peanuts showed no degradation in quality or sensory acceptability, and have the flavor and aroma of natural whole peanuts. Hypoallergenic or non-allergenic peanuts produced in accordance with the present invention may be used as ingredients in various food products and other edible materials.

11 Claims, 1 Drawing Sheet the SDS-PAGE of peanut protein extracts from enzyme treated peanut kernels. Lane 1-raw control, 2-raw-0.12%-1 hr, 3-raw-0.12%-3 hr, 4-roasted–control, 5-roasted-0.12%-1 hr, 6-roasted-0.12%-3hr, 7-roasted-soaking only

OTHER PUBLICATIONS

Neucere et al. "Effect of Heat on Peanut Proteins II. Variations in Nutritional Quality of the Meals" 1972 Journal of Agricultural Food Chemistry, vol. 20, No. 2 (pp. 256-259).*

Kopper et al. "Peanut protein allergens: Gastric digestion is carried out exclusively by pepsin" 2004 Journal of Allergy Clinical Immunology 2004 vol. 114, p. 614-8.*

Matthias Besler et al. Stability of food allergens and allergenicity of processed foods (2001) Journal of Chromatography B, 756 pp. 207-228.*

Food and Agricultural Industry Peanut Processing 9.10.2.2 1995 http://www.epa.gov/ttnchie1/ap42/ch09/final/c9s10-2b.pdf 6 pages.*

Thanakorn Weangsripanaval, Tatsuya Moriyama, Tadashi Kageura, Tadashi Ogawa and Teruo Kawada, Dietary Fat and an Exogenous Emulsifier Increase the Gastrointestinal Absorption of a Major Soybean Allergen, Gly m Bd 30K, in Mice, journal, Copyright 2005, pp. 1738-1744, American Society for Nutritional Sciences.

E.N.C. Mills, C. Madsen, P.R. Shewry and H.J. Wichers, Food Allergens of Plant Origin—Their Molecular and Evolutionary Relationships, journal, Copyright 2003, pp. 145-156, Elsevier Science Ltd.

Soheila J. Maleki, Randall A. Kopper, David S. Shin, Chun-Wook Park, Cesar M. Compadre, Hugh Sampson, A. Wesley Burks and Gary A. Bannon, Structure of the Major Peanut Allergen Ara h 1 May Protect IgE-Binding Epitopes from Degradation, journal, Copyright 2000, pp. 5844-5849, The American Association of Immunologists.

International Search Report mailed on Oct. 30, 2008 in PCT/US2008/065881.

T. Eiwegger et al., "Gastro-duodenal digestion products of the major peanut allergen Ara h 1 retain an allergenic potential," copyright 2006, pp. 1281-1288, vol. 36, Clinical and Experimental Allergy.

Written Opinion mailed on Oct. 30, 2008 in PCT/US2008/065881.

Kirsten Beyer, M.D. et al., "Food and drug reactions and anaphylaxis—Effects of cooking methods on peanut allergenicity," copyright 2001, Journal of Allergy and Clinical Immunology, vol. 107, No. 6, pp. 1077-1081.

M.L. Kakade et al., "Determination of Trypsin Inhibitor Activity of Soy Products: A Collaborative Analysis of an Improved Procedure," copyright 1974, American Association of Cereal Chemists, Inc., pp. 376-382.

Soheila J. Maleki, Ph.D. et al., "The major peanut allergen, Ara h 2, functions as a trypsin inhibitor, and roasting enhances this function," copyright 2003, Journal of Allergy and Clinical Immunology, vol. 112, No. 1, pp. 190-195.

U.S. Appl. No. 12/631,325, filed Dec. 4, 2009, Ahmedna et al.

S.J. Koppelman et al., "Quantification of major peanut allergens Ara h 1 and Ara h 2 in the peanut varieties Runner, Spanish, Virginia, and Valencia, bred in different parts of the world," copyright 2001, Allergy, vol. 56, pp. 132-137.

Soheila J. Maleki, Ph.D. et al., "The effects of roasting on the allergenic properties of peanut proteins," copyright 2000, Journal of Allergy and Clinical Immunology, vol. 106, No. 4, pp. 763-768.

Soheila Maleki et al., "Structure of the Major Peanut Allergen Ara h1 May Protect IgE-Binding Epitopes from Degradation," copyright 2000, Journal of Immunology, vol. 164, pp. 5844-5849.

E.N.C. Mills et al., "Food allergens of plant origin—their molecular and evolutionary relationships," copyright 2003, Trends in Food Science and Technology, vol. 14, pp. 145-156.

Amy M. Scurlock, M.D., et al., "Peanut allergenicity," copyright 2004, Annals of Allergy, Asthma & Immunology, vol. 93, pp. S12-S18.

The Allergen Nomenclature Subcommittee of the International Union of Immunological Societies, copyright 2009, web page, www.allergen.org/Allergen.aspx.

Hsiao-Wei Wen et al., "Peanut Allergy, Peanut Allergens, and Methods for the Detection of Peanut Contamination in Food Products," copyright 2007, Comprehensive Reviews in Food Science and Food Safety, vol. 6, pp. 47-58.

Kopper et al., "Peanut Protein Allergens: The Effect of Roasting on Solubility and Allergenicity," copyright 2005, International Archives of Allergy and Immunology, vol. 136(1), pp. 16-22.

Astwood, J.O., et al., "Stability of food allergens to digestion in vitro," Copyright 1996, Nature Biotechnology, vol. 14, pp. 1269-1273.

Bannon, G.A., et al., "Engineering Characterization and in vitro Efficacy of the Major Peanut Allergens for Use in Immunotherapy," Copyright 2001, International Archives of Allergy and Immunology, vol. 124, pp. 70-72.

Bannon, G.A., et al., "Protein Digestibility and Relevance to Allergenicity," Copyright 2003, Environmental Health Perspective, vol. 111, No. 8, pp. 1122-1124.

Beyer, K., MD. et al., "Food and drug reactions and anaphylaxis—Effects of cooking methods on peanut allergenicity," Copyright 2001, Journal of Allergy and Clinical Immunology, vol. 107, No. 6, pp. 1077-1081.

Cabanillas, B., et al., "Effects of Autoclaving on Allergenicity of Roasted Peanut," Copyright 2009, Journal of Allergy and Clinical Immunology, Abstract, vol. 123, No. 2, S31.

Chiou, R.Y.Y. and Tsai, T.T., "Characterization of peanut proteins during roasting as affected by initial moisture content," Copyright 1989, Journal of Agricultural and Food Chemistry, vol. 37, pp. 1377-1381.

Chu, Y., et al., "Reduction of IgE Binding and Nonpromotion of Aspergillus flavus Fungal Growth by Simultaneously Silencing Ara h 2 and Ara h 6 in Peanut," Copyright 2008, Journal of Agricultural and Food Chemistry, vol. 56, pp. 11225-11233.

Chung, S.-Y. and Champagne, E.T., "Reducing the allergenic capacity of peanut extracts and liquid peanut butter by phenolic compounds," Copyright 2009, Food Chemistry, vol. 115, pp. 1345-1349.

Guo, B.Z., et al., "Proteomic Analysis of Peanut Seed Storage Proteins and Genetic Variation in a Potential Peanut Allergen," Copyright 2008, Protein Peptide Letters, vol. 15, pp. 567-577.

Herman, E.M., et al., "Genetic Modification Removes an Immunodominant Allergen from Soybean," Copyright 2003, Plant Physiology, vol. 132, pp. 36-43.

Kagan, R.S., et al., "Prevalence of peanut allergy in primary school in Montreal, Canada," Copyright 2003, Journal of Allergy and Clinical Immunology, vol. 112, pp. 1223-1228.

Kakade, M. et al., "Determination of Trypsin Inhibitor Activity of Soy Products: A Collaborative Analysis of an Improved Procedure," Copyright 1974, American Association of Cereal Chemists, Inc., pp. 376-382.

Koppelman, S.J., et al., "Relevance of Ara h 1, Ara h 2 and Ara h 3 in peanut allergic patients, as determined by immunoglobulin E Western blotting, basophil-histamine release and intracutaneous testing: Ara h 2 is the most important peanut allergen," Copyright 2004, Clinical and Experimental Allergy, vol. 34, pp. 583-590.

Maleki, S.J., et al., "The major peanut allergen, Ara h2, functions as a trypsin inhibitor, and roasting enhances this function," Copyright 2003, Journal of Allergy and Clinical Immunology, vol. 112, pp. 190-195.

Mondoulet, L., et al., "Influence of Thermal Processing on the Allergenicity of Peanut Proteins," Copyright 2005, Journal of Agricultural and Food Chemistry, vol. 53, pp. 4547-4553.

Norioka, S., et al., "Purification and Characterization of Protease Inhibitors from Peanuts (*Arachis hypogaea*)," Copyright 1982, Journal of Biochemistry, vol. 91, pp. 1427-1434.

Palmer, G.W., et al., "Comparative potency of Ara h1 and Ara h2 in immunochemical and functional assays of allergenicity," Copyright 2005, Clinical Immunology, vol. 115, pp. 302-312.

Perkins, D. and Toledo, R.T., "Effect of Heat Treatment for Trypsin Inhibitor Inactivation on Physical and Functional Properties of Peanut Protein," Copyright 1982, Journal of Food Science, vol. 47, pp. 917-923.

Sampson, H.A., "Update on food allergy," Copyright 2004, Journal of Allergy and Clinical Immunology, vol. 113, pp. 805-819.

Schmitt, D.A., et al., "Competitive Inhibition ELISA for Quantification of Ara h 1 and Ara h 2, the Major Allergens of Peanuts," Copyright 2004, Journal of AOAC International, vol. 87, pp. 1492-1497.

Schmitt, D.A., et al., "Processing Can Alter the Properties of Peanut Extract Preparations," Copyright 2010, Journal of Agricultural and Food Chemistry, vol. 58, pp. 1138-1143.

Sen, M., et al., "Protein Structure Plays a Critical Role in Peanut Allergen Stability and May Determine Immunodominant IgE-Binding Epitopes," Copyright 2002, Journal of Immunology, vol. 169, pp. 882-887.

Sicherer, S.H. and Sampson, H.A., "Peanut allergy: Emerging concepts and approaches for an apparent epidemic," Copyright 2007, Journal of Allergy and Clinical Immunology, vol. 120, pp. 491-503.

Sicherer, S.H., et al., "Prevalence of peanuts and tree nuts allergy in the United States determined by means of a random digit dial telephone survey: A 5-year follow-up study," Copyright 2003, Journal of Allergy and Clinical Immunology, vol. 112, pp. 1203-1207.

Watanabe, M., "Hypoallergenic rice as a physiologically functional food," Copyright 1993, Trends in Food Science and Technology, vol. 4, pp. 125-128.

Whitaker, J. R., "Proteolytic Enzymes," Copyright 2003, in J. R. Whitaker, A. J. Voragen, & D.W. S. Wong (Eds.), Handbook of food enzymology, New York: Marcel Dekker, Inc.

Yu, J. et al., "Enzymatic treatment of peanut kernels to reduce allergen levels," Copyright 2011, Food Chemistry, vol. 127, Issue 3, pp. 1014-1022.

Ahmedna et al., U.S. Appl. No. 12/631,325, Office Action dated Jan. 19, 2012.

* cited by examiner

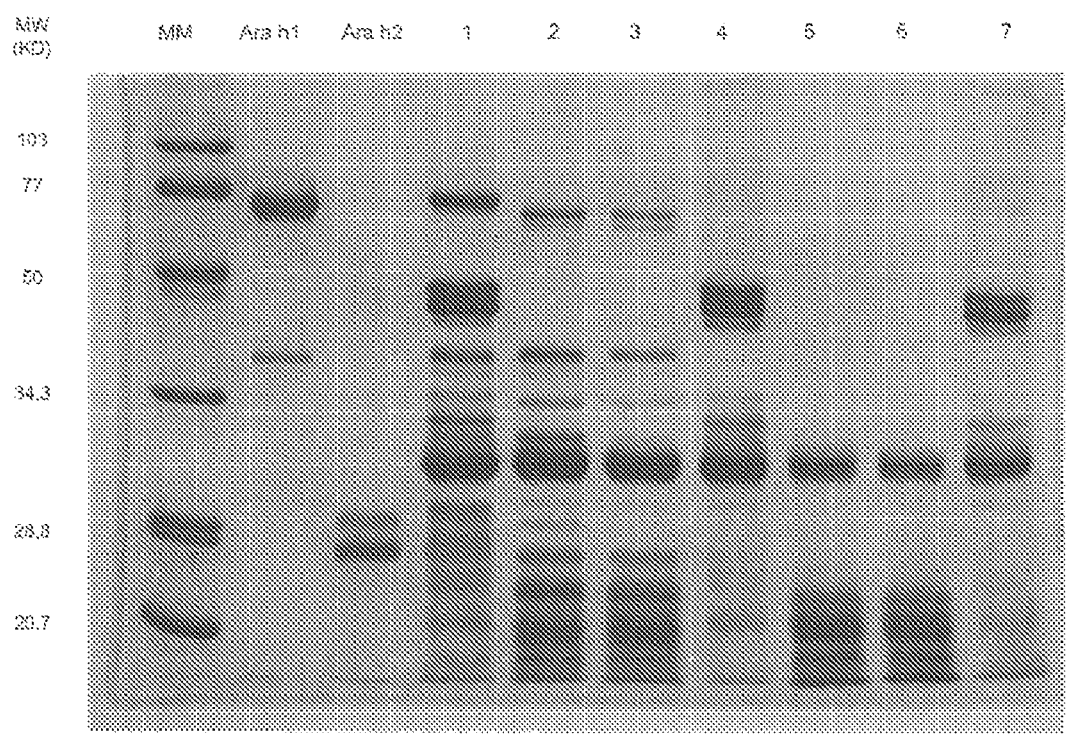
the SDS-PAGE of peanut protein extracts from enzyme treated peanut kernels. Lane 1-raw control, 2-raw-0.12%-1 hr, 3-raw-0.12%-3 hr, 4-roasted –control, 5-roasted-0.12%-1 hr, 6-roasted-0.12%-3hr, 7-roasted-soaking only

PROCESS FOR PREPARING HYPOALLERGENIC AND NON-ALLERGENIC PEANUTS (*ARACHIS HYPOGAEA*) UTILIZING AN ENDOPEPTIDASE

FIELD OF THE INVENTION

The present invention relates to a simple and inexpensive method for substantially reducing, or completely eliminating, the allergenicity of the peanut (*Arachis hypogea*) by directly applying a hypoallergenically-effective amount of a solution comprising at least one endopeptidase to raw, blanched, or roasted peanuts, or peanut products or derivatives (including, but not limited to, peanut kernels, peanut skins, peanut protein isolate, peanut flour, or peanut milk) produced from raw, blanched, or roasted peanuts. The endopeptidase-treated peanuts have the flavor and aroma of natural whole peanuts, but the allergens which cause allergic reactions in the majority of those people who suffer from peanut allergies, have been either substantially (i.e., greater than about 30%) reduced or completely (100%) eliminated.

BACKGROUND OF THE INVENTION

Many persons suffer from various allergies, several of which are caused by ingesting foods containing allergens, which are usually proteins. Although the biochemistry of allergic reactions is not precisely understood, it is believed that proteinaceous allergens cause, upon ingestion or other contact with the human body, a specific reagin to be formed in the blood. The ability to produce reagins, chemically identified as IgE, in response to a given allergen is thought to be an inherited characteristic that differentiates an allergic person from a non-allergic person. The specificity of the allergen-reagin reaction is similar to the antigen-antibody reaction.

It has been estimated that ~8% of children and 2% of adults have allergic reactions to food (Weangsripanaval et al., Journal of Nutrition: 2005, 1738-1744). Many common foods contain various allergens, and food allergy is common in both adults and children. Foods which are generally regarded as being particularly allergenic include chocolate, nuts, milk and milk byproducts, wheat, eggs, corn, pork, soybeans, tomatoes, oranges, crustaceans, rice, seafood, fish spices, condiments, wine, and other products of fermentation. Symptoms of food allergy range from mild to severe, and can include allergic skin eruptions, respiratory tract allergy (allergic rhinitis and asthma), gastrointestinal reactions, shock-like reactions, vascular collapse, and allergic anaphylaxis.

Peanuts are a very frequently consumed and popular food product. However, allergists have long-recognized that peanuts contain allergens. In fact, the peanut allergens are among the most severe common allergens, and have been referred to as "super allergens" because they account for at least 70% of severe anaphylactic reactions. Many studies have been done to characterize the special proteins responsible for peanut allergies. At least seven peanut allergens, belonging to three super protein families (Mills et al., Trends in Food Science & Technology 14: 145-46, 2003), have presently been identified and are classified as Ara h1 to Ara h8. Ara h2, Ara h6, and Ara h7 are 2S albumins with molecular weights between 3-9,000 Dalton; Ara h1, a 7S globulin, with a molecular weight between 50-70,000 Dalton; and Ara h3 and Ara h4, 7S globulins, with molecular weights between 30-40,000 Dalton. The common feature of these allergens is that they show unusually high stability to denaturation and proteolysis, a property that may contribute to their high allergenicity. The two major peanut allergens are seed storage proteins known as Ara h1, a member of the vicilin family, and Ara h2, a conglutin-homologue protein. These two allergens are recognized by serum IgE from >90% of peanut allergic patients (Maleki et al., Journal of Immunology: 2000, 164, 5844-5849).

Although peanuts are most often consumed raw, blanched (boiled for a short period of time), or roasted, or in the form of peanut butter, peanut milk, or peanut flour, and may thus be easily avoided by sensitive individuals, the myriad of hidden ways in which peanuts are used make it difficult to avoid all contact. For example, peanut oil, peanut butter, and peanut flour are very frequently used as ingredients in popular food products such as candy, ethnic foods, hydrogenated oils, margarine, vegetable burgers, spaghetti sauce, and chili. In addition, food products that normally do not contain peanuts or peanut products are frequently cross-contaminated with peanuts because the same machinery is often used to prepare several different food products. Contamination may also be picked up from storage bins.

The food industry has voluntarily adopted stringent regulations for the clean-up and labeling of peanut allergen-containing foods. Significant efforts and costs are expended each year in the recall of foods suspected to contain traces of peanut allergens. Accordingly, there exists a great need for a hypoallergenic peanut, both to improve food safety and to permit allergic individuals to enjoy this common and nutritious food. Accordingly, there is a need for a hypoallergenic food containing peanuts or peanut products, particularly one which has the taste and aroma of fresh peanuts.

Advantageously, the inventors have discovered that direct treatment of peanuts or peanut derivatives with a solution containing at least one endopeptidase in the manner described below can either substantially reduce (i.e., greater than about 30%) or completely eliminate allergenic activity, as indicated by immunoassays.

SUMMARY OF THE INVENTION

The present invention provides a clean, simple, and inexpensive method for substantially (i.e., greater than about 30%) reducing or completely (100%) eliminating the allergenic activities of allergenic proteins by direct application of a hypoallergenically-effective amount of a solution containing at least one endopeptidase to either raw, blanched, or roasted peanuts, or peanut products or derivatives (including, but not limited to peanut flour, peanut skins, peanut protein isolate, or peanut milk) produced from raw, blanched, or roasted peanuts. In an aspect of an embodiment of the present invention, the hypoallergenically-effective amount of the endopeptidase in solution is at least about 0.001% (w/w). In another aspect of an embodiment, a new and useful hypoallergenic food product is produced to contain peanuts or peanut products, including, but not limited to, peanut flour, peanut butter, peanut milk, peanut kernel-based snacks, and peanut protein isolate. In another aspect of an embodiment of the present invention, the substantial (i.e., greater than about 30%) reduction or complete (100%) elimination of allergenic activities is achieved in peanuts without destroying taste, aroma, and flavor. It is a further aspect of an embodiment of this invention to substantially reduce or completely eliminate allergenic activities in peanuts and peanut products quickly, simply, safely, and at relatively low cost.

BRIEF DESCRIPTION OF THE FIGURES

The present invention is better understood by a reading of the Detailed Description of the Invention along with a review of the drawings, in which:

FIG. 1 is the SDS-PAGE of peanut protein extracts from enzyme treated peanut kernels.

DETAILED DESCRIPTION OF THE INVENTION

The following definitions are provided in order to aid those skilled in the art in understanding the detailed description of the present invention. Some words and phrases may also be defined in other sections of the specification. No limitation should be placed on the definitions presented for the terms below, where other meanings are evidenced elsewhere in the specification in addition to those specified below.

For purposes of the present invention, the term "allergen" refers to a biological or chemical substance that induces an allergic reaction or response. An allergic reaction can be an immunoglobin (Ig) E-mediated response. The term "IgE" (Immunoglobin E) refers to a specific class of immunoglobin secreted by B cells. IgE binds to specific receptors on Mast cells. Interaction of an allergen with Mast cell-bound IgE may trigger allergic symptoms.

For purposes of the present invention, the term "hypoallergenic" means a decreased tendency to cause an allergic reaction through the substantial (i.e., greater than about 30%) reduction or complete (100%) elimination of activity of allergenic proteins.

For purposes of the present invention, the term "peanut" means the edible portion of a peanut, whether raw, blanched (boiled for a short period of time), or roasted, or in kernel, milk, protein isolate, or flour form.

For the purposes of the present invention, the term "serine endopeptidase" (or serine protease) means any proteolytic enzyme that is characterized by the presence of a serine residue in the active site of the enzyme.

It has been discovered that the direct treatment of either raw, blanched, or roasted peanuts, or peanut products or derivates (including, but not limited to peanut butter, peanut flour, peanut protein isolate, peanut skins, or peanut milk) produced from raw, blanched, or roasted peanuts, with a solution containing at least about 0.001% (w/w) of at least one endopeptidase substantially reduces or completely eliminates the activity of peanut allergens. Examples of suitable endopeptidases that may be used in accordance with an aspect of the present invention include, but are not limited to, pepsin, trypsin, and α-chymotrypsin, although it is envisioned that any endopeptidase that hydrolyzes proteins in a similar manner can be utilized in the methods disclosed and claimed in the present invention. In one aspect of an embodiment of the present invention the endopeptidase is a serine endopeptidase. The endopeptidase may also be used alone or in combination with another endopeptidase, or with one or more proteolytic or non-proteolytic enzymes, including, but not limited to esterase, esterase lipase, α-galactoside, α-glucosidase, and α-manosidase. In one aspect of an embodiment of the present invention the endopeptidase solution contains from about 0.001 to about 0.5% pepsin. In another aspect of an embodiment, the endopeptidase solution contains from about 0.001% to about 0.5% trypsin. In a further aspect of an embodiment the endopeptidase solution contains from about 0.001% to about 0.5% α-chymotrypsin. Depending on the concentration of endopeptidase used in the solution, and the particular endopeptidase used, peanut allergens can be substantially reduced or completely inactivated after as little as about 15 minutes (0.25 hrs) of treatment.

Other than in the operating examples, or where otherwise indicated, all numbers below expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The hypoallergenic peanuts according to an aspect of an embodiment of the present invention are prepared by treating peanuts, which may be raw, roasted, or blanched, or whole, or in the form of peanut kernels, or in the form of a peanut product or derivative (including, but not limited to, peanut milk, peanut skins, peanut protein isolate, or peanut flour prepared from grinding peanuts), with a solution containing at least about 0.001% (w/w) of at least one endopeptidase. The peanuts may be either raw (unroasted), blanched, or roasted, but a greater reduction in the concentration of allergenic proteins has been observed when the peanuts are roasted. In addition, prior to enzyme treatment, the raw, blanched, or roasted peanuts may be heat-treated. In one aspect of an embodiment, both raw and roasted peanuts are heat-treated by being blanched in boiling water for at least five minutes but, any other heat-treatment methods sufficient to inactivate microorganisms and loosen the kernel structure for enzyme distribution may be utilized. Data indicates that prior blanching of roasted peanuts enhances the effectiveness of the endopeptidase enzyme in inactivating peanut allergens.

Following heat-treatment, the peanut kernels may be left in kernel form or ground into peanut flour.

A solution containing at least about 0.001% (w/w) of at least one endopeptidase is then added to the peanut kernels or flour, or peanut skin, or protein isolate. These endopeptidase enzymes may be bacterial, fungal, animal, plant, or recombinant in origin. Furthermore, these enzymes, either alone or in combination with other proteolytic or endopeptidase enzymes, may be added to the peanuts or peanut derivatives in either a continuous or a batch process. In one aspect of an embodiment of the present invention, a solution containing a single endopeptidase in which the concentration of the endopeptidase is at least about 0.001% (w/w) is utilized. Generally, however, the use of an endopeptidase solution in which the concentration of endopeptidase is greater than about 0.1% (w/w) yields a higher reduction in the levels of or complete elimination of peanut allergens, regardless of time of exposure.

In one aspect of one embodiment, trypsin, alone, at a pH in the range from about 6-11, and at a concentration in the range from about 0.001% to about 0.5% is utilized to treat peanut kernels. In another aspect of an embodiment, the trypsin is buffered to a pH of 8 and used at a concentration in the range of between about 0.1% and about 0.2%. In another aspect of an embodiment of the present invention, pepsin, alone, at a pH in the range of about 1-3 and at a concentration in the range from about 0.001% to about 0.5% is utilized. In a further aspect of an embodiment, the pepsin is buffered to a pH of 2 and used at a concentration in the range of between about 0.1% and about 0.2%. In yet another aspect of an embodiment of the present invention, α-chymotrypsin, alone, is used, at a pH in the range from about 6-11 and at a concentration in the range of between about 0.001% to about 0.5%. In a further aspect of an embodiment, the α-chymotrypsin is buffered to a pH of 8 and used at a concentration between about 0.1% and about 0.2%.

Following application of the enzyme solution, the peanuts or peanut products or derivates are incubated at a temperature sufficient to allow enzyme activity to take place and for a period of time sufficient to allow the enzyme to inactivate the allergens. In aspect of one embodiment of the present invention, the enzyme-treated peanut kernels are incubated at a temperature in the range from between about 20° C. to about 50° C. for about 0.25 hours to about 8 hours. In a further aspect of an embodiment, the treated peanut kernels or flour are kept at a temperature of about 37° C.

Following enzyme treatment, the peanuts are separated from the enzyme solution and then treated to inactivate any residual enzyme activity. Any method of inactivating enzymes may be utilized, but in one aspect of an embodiment the peanuts are dried at a temperature greater than about 60° C. Methods of drying include, but are not limited to, regular oven drying, vacuum oven drying, drum drying, freeze drying, spray drying, or sun drying. In one aspect of an embodiment of the present invention the peanuts are removed from the enzyme solution and dried in a preheated vacuum oven at a temperature of about 65-70° C. overnight.

Measurements of concentrations of the two major allergenic proteins, Ara h1 and Ara h2, were used to indicate the reduction in activity of all peanut allergens.

It has been observed that the enzyme treatment has no significant effect on either the taste or aroma of the hypoallergenic peanuts produced in accordance with the present invention. Thus, the hypoallergenic peanuts according to an aspect of an embodiment of the present invention smell and taste substantially like regular, or non-hypoallergenic, peanuts. Accordingly, the hypoallergenic peanuts produced in accordance with an aspect of an embodiment of present invention may be used in instances where regular peanuts are presently used.

Aspects of embodiments of the present invention will now be described in more detail with reference to the following, specific, non-limiting examples:

EXAMPLES

Example 1

Effect of α-Chymotrypsin on Heat-Treated (Blanched) and Non-Heat-Treated Peanuts In one example, the endopeptidase α-chymotrpysin was tested for its effectiveness in reducing the allergenic activity of both heat-treated and non-heat-treated peanut kernels. Measurements of concentrations of the two major allergenic proteins, Ara h1 and Ara h2, were used to indicate the reduction in activity of all known peanut allergens (e.g., Ara h1 to Ara h8).

Procedure—Unroasted (raw) or roasted peanut kernels were heat-treated by being blanched in boiling water for about 5 minutes and then cooled to about room temperature. Other peanut kernels, both raw and roasted, were used without prior heat-treatment. Samples containing either blanched unroasted, blanched roasted, non-blanched unroasted, and non-blanched roasted peanut kernels were immersed in a solution containing α-chymotrypsin, wherein the enzyme concentration was 0.01%, 0.05%, 0.10% and 0.15% (w/w), respectively. The solutions containing the peanut kernels were then incubated at a temperature of about 37° C. for 1, 3, and 5 hours, respectively. The enzyme-containing peanut kernels were dried at about 65-70° C. in a preheated vacuum oven overnight. The dried kernels were then ground into flour using a high-speed blender.

Extraction of peanut protein—One gram of peanut flour from each treatment was mixed with about 20 ml of Tris HCl buffer (pH 8.3) and stirred at room temperature for about 2 hours. Mixtures were then centrifuged at about 3,000 g for about 20 minutes. The lipid layer on top of the supernatant was removed using transfer pipettes and supernatant was stored at about −20° C. for future analysis.

Determination of soluble protein in extracts—Soluble protein in each extract was determined by bicinchoninic acid (BCA) method using bovine serum albumin (BSA) as standard. Peanut protein extracts were diluted about 5-10 times with deionized water to bring the protein concentration of the test samples within the linear rage of BSA calibration curve (0-1.0 mg/ml).

Determination of Ara h1 and Ara h2—A direct ELISA method was used to determine Ara h1 and Ara h2 in peanut extracts from treated and untreated peanut kernels, using chicken anti-Ara h1 and anti-Ara h2 as the primary antibodies and peroxidase labeled anti-chicken antibody as the detection antibody. ABTS as enzyme substrate was used for spectrometric detection of allergens. Purified Ara h1 and Ara h2 (provided by Dr. Melaki, USDA-ARS) were used as positive controls and in developing standard curves used in quantitation. Final results were calculated as mg Ara h1 and mg Ara h2 per gram of soluble protein.

SDS-PAGE—Sodium dodecyl sulfate polyacrimide gel electrophoresis (SDS-PAGE) was used as a confirmation method for the breakdown of allergens or absence of allergenic concentrations. Depending on the protein concentration of each peanut protein extract, as determined by BCA method, extracts were diluted quantitatively to a protein concentration of about 1.0 mg/ml with SDS-PAGE buffer, then boiled at about 90° C. for about 10 minutes to completely denature the proteins. After cooling to room temperature, samples were loaded on a polyacrylamide gel (10 μl/well). The gel was then resolved using a Bio-Rad Mini-Protein gel electrophoresis system. Following staining, bands were identified using molecular weight markers and purified Ara h1 and Ara h2. (See FIG. 1.)

Results—Preliminary results showed that α-chymotrypsin demonstrated significant activity with respect to Ara h1 and Ara h2 inactivation.

TABLE 1

Changes in soluble protein of peanut kernels after treatment with α-chymotrypsin

| Treatment | | Soluble protein (mg/ml) | |
| --- | --- | --- | --- |
| Enzyme Concentration | Time | Raw | Roasted |
| Control (0%) | 0 | 7.029 ± 0.016 | 2.30 ± 0.02 |
| 0.010% | 1 | 4.484 ± 0.100 | 2.58 ± 0.01 |
| | 3 | 4.476 ± 0.065 | 2.79 ± 0.02 |
| | 5 | 5.079 ± 0.020 | 2.74 ± 0.05 |
| 0.050% | 1 | 5.049 ± 0.079 | 3.96 ± 0.10 |
| | 3 | 4.921 ± 0.041 | 4.20 ± 0.00 |
| | 5 | 4.768 ± 0.002 | 3.86 ± 0.01 |

TABLE 1-continued

Changes in soluble protein of peanut kernels after
treatment with α-chymotrypsin

| Treatment | | Soluble protein (mg/ml) | |
|---|---|---|---|
| Enzyme Concentration | Time | Raw | Roasted |
| 0.100% | 1 | 5.254 ± 0.061 | 4.14 ± 0.03 |
| | 3 | 5.272 ± 0.124 | 4.12 ± 0.05 |
| | 5 | 5.150 ± 0.116 | 4.03 ± 0.02 |
| 0.150% | 1 | 6.13 ± 0.00 | 4.91 ± 0.09 |
| | 3 | 6.34 ± 0.00 | 4.56 ± 0.01 |
| | 5 | 6.41 ± 0.09 | 4.85 ± 0.00 |

Table 1 shows that, after treatment of raw peanut kernels with a solution containing α-chymotrypsin, and subsequent drying, soluble protein decreased compared to untreated samples. However, comparison of the protein concentrations of all extracts from α-chymotrypsin-treated raw peanut kernels revealed that soluble protein actually increased with increasing enzyme concentration. Even at low concentrations of α-chymotrypsin (about 0.01%), soluble protein concentration increased with treatment time. Therefore, treatment with α-chymotrypsin was effective in increasing protein solubility of peanuts. Without wishing to be bound to a particular theory, the effectiveness was probably due to proteolytic breakdown of the proteins in the peanuts into smaller, more soluble proteins. Moreover, the lower protein concentrations in extracts from raw peanut kernels treated with low concentrations of α-chymotrypsin solution could be attributed to the drying step following enzyme treatment. Such a step could have partially denatured the native proteins in the raw peanuts. The same heat effect is also believed to be responsible for the low solubility in untreated (control) roasted peanuts compared to raw peanuts. However, enzyme treatment significantly increased soluble protein concentration in roasted peanut kernels for all treated samples, with higher concentrations of α-chymotrypsin yielding higher protein solubility in the kernels. Overall, the effect of treatment time on soluble protein concentration was less significant than that of protein concentration. Based on SDS-PAGE results, the increased protein solubility in peanut kernels treated with solutions of α-chymotrypsin seems to correspond to the disappearance of allergen bands and increased intensities of low molecular weight protein bands in the gels of treated peanuts.

Effects of Treatment by α-Chymotrypsin on Non-Blanched Raw and Roasted Peanut Kernels

TABLE 2

Allergen changes in non-blanched raw peanut kernels
after treatment with α-chymotrypsin

| Enzyme Concentration | Time hr | Protein (mg/ml) | Ara h1 (mg/g protein) | Ara h2 (mg/g protein) | % Ara h1 change | % Ara h2 change |
|---|---|---|---|---|---|---|
| 0.01% | 1 | 7.02 | 3.60 ± 0.14 | 0.51 ± 0.04 | −4 | −48 |
| | 3 | 6.28 | 4.09 ± 0.18 | 0.59 ± 0.06 | +9 | −40 |
| | 5 | 6.05 | 3.97 ± 0.16 | 0.49 ± 0.07 | +6 | −50 |
| 0.05% | 1 | 6.99 | 2.96 ± 0.18 | 0.28 ± 0.03 | −21 | −71 |
| | 3 | 6.80 | 3.03 ± 0.29 | 0.27 ± 0.04 | −19 | −72 |
| | 5 | 6.34 | 3.20 ± 0.21 | 0.25 ± 0.02 | −15 | −75 |
| 0.10% | 1 | 6.82 | 2.82 ± 0.23 | 0.26 ± 0.06 | −25 | −73 |
| | 3 | 6.70 | 3.03 ± 0.28 | 0.25 ± 0.07 | −19 | −74 |
| | 5 | 6.33 | 3.10 ± 0.18 | 0.23 ± 0.07 | −17 | −77 |
| 0.15% | 1 | 6.49 | 2.85 ± 0.27 | 0.23 ± 0.03 | −24 | −77 |
| | 3 | 6.80 | 2.32 ± 0.18 | 0.17 ± 0.02 | −38 | −83 |
| | 5 | 6.41 | 3.25 ± 0.18 | 0.23 ± 0.02 | −13 | −76 |

Table 2 illustrates the effects of treatment of non-blanched raw peanut kernels by α-chymotrypsin on Ara h1 and Ara h2 concentrations. Data suggest that Ara h1 in non-blanched raw peanut kernels was more resistant to α-chymotrypsin activity than Ara h2. The treatment of non-blanched raw peanut kernels by low concentrations (about 0.01%) α-chymotrypsin solutions did not lower the concentration of Ara h1, but instead seemed to increase it slightly, possibly due to partial denaturation from the heat of drying of the non-blanched raw peanut kernels after enzyme treatment. Treated kernels were dried at a temperature of about 70° C. in order to inactivate the enzyme. Without wishing to be bound to a particular theory, this heat may have exposed more antibody binding sites while the α-chymotrypsin concentration was too low to make a difference.

Ara h2 in non-blanched raw peanut kernels exhibited more sensitivity to α-chymotrypsin. At an enzyme concentration of about 0.01% there was about a 40-50% reduction of Ara h2 in non-blanched raw peanuts, but when the enzyme concentration increased to about 0.05%, the reduction of Ara h2 increased to about 71-75%.

TABLE 3

Allergen changes in non-blanched roasted peanut kernels after α-chymotrypsin treatment

| Enzyme Concentration | Time hr | Protein (mg/ml) | Ara h1 (mg/g protein) | Ara h2 (mg/g protein) | % Ara h1 change | % Ara h2 change |
|---|---|---|---|---|---|---|
| 0.01% | 1 | 4.10 | 0.91 ± 0.03 | 0.47 ± 0.03 | −63 | −39 |
|       | 3 | 4.05 | 0.52 ± 0.02 | 0.33 ± 0.02 | −79 | −57 |
|       | 5 | 4.21 | 0.41 ± 0.03 | 0.27 ± 0.01 | −83 | −65 |
| 0.05% | 1 | 3.49 | 0.26 ± 0.04 | 0.29 ± 0.07 | −90 | −63 |
|       | 3 | 3.62 | 0.13 ± 0.01 | 0.23 ± 0.01 | −95 | −70 |
|       | 5 | 3.53 | 0.22 ± 0.02 | 0.19 ± 0.01 | −91 | −76 |
| 0.10% | 1 | 3.79 | 0.19 ± 0.02 | 0.11 ± 0.01 | −92 | −86 |
|       | 3 | 4.07 | 0.12 ± 0.03 | 0.12 ± 0.01 | −95 | −85 |
|       | 5 | 3.79 | 0.14 ± 0.01 | 0.09 ± 0.00 | −94 | −89 |
| 0.15% | 1 | 3.91 | 0.14 ± 0.03 | 0.12 ± 0.02 | −94 | −85 |
|       | 3 | 3.70 | 0.12 ± 0.02 | 0.12 ± 0.00 | −95 | −85 |
|       | 5 | 4.07 | 0.23 ± 0.05 | 0.11 ± 0.05 | −91 | −86 |

Table 3 shows the effect of treatment of non-blanched roasted peanut kernels by α-chymotrypsin. The results demonstrated that the activities of both Ara h1 and Ara h2 were affected by α-chymotrypsin. At equal treatment times, higher concentrations of α-chymotrypsin resulted in higher reductions in the activities of both Ara h1 and Ara h2, while at equal enzyme concentration, longer treatment time resulted in higher reduction of the activities of both allergens.

Effects of Treatment by α-Chymotrypsin on Blanched Raw and Roasted Peanut Kernels Both raw and roasted peanut kernels were blanched in boiling water for about 5 minutes before treatment with α-chymotrypsin. Without wishing to be bound by any particular theory, it is believed that blanching inactivates microorganisms on the surface of the peanut kernels and loosens the structure of the kernels in order to facilitate the rapid penetration of the peanut kernel by the enzyme and to increase its effectiveness.

TABLE 4

Allergen changes in blanched raw peanut kernels after α-chymotrypsin treatment

| Enzyme Concentration | Time hr | Protein (mg/ml) | Ara h1 (mg/g protein) | Ara h2 (mg/g protein) | % Ara h1 change | % Ara h2 change |
|---|---|---|---|---|---|---|
| 0.01% | 1 | 4.48 | 5.58 ± 0.11 | 3.01 ± 0.13 | +62 | +207 |
|       | 3 | 4.75 | 5.70 ± 0.29 | 2.65 ± 0.16 | +66 | +171 |
|       | 5 | 5.08 | 4.97 ± 0.29 | 2.18 ± 0.24 | +44 | +122 |
| 0.05% | 1 | 5.05 | 3.97 ± 0.27 | 1.75 ± 0.16 | +15 | +79 |
|       | 3 | 4.92 | 4.66 ± 0.57 | 1.93 ± 0.05 | +35 | +97 |
|       | 5 | 4.77 | 4.31 ± 0.20 | 2.01 ± 0.06 | +25 | +105 |
| 0.10% | 1 | 5.25 | 3.03 ± 0.31 | 1.03 ± 0.02 | −12 | +5 |
|       | 3 | 5.27 | 3.29 ± 0.20 | 1.31 ± 0.06 | −5 | +34 |
|       | 5 | 5.15 | 2.74 ± 0.14 | 1.20 ± 0.03 | −21 | −23 |
| 0.15% | 1 | 6.13 | 1.99 ± 0.14 | 0.51 ± 0.01 | −42 | −48 |
|       | 3 | 6.34 | 2.04 ± 0.16 | 0.62 ± 0.04 | −41 | −37 |
|       | 5 | 6.41 | 2.31 ± 0.13 | 0.60 ± 0.08 | −33 | −39 |

Table 4 shows that when the concentration of α-chymotrypsin was in the range of about 0.01 to 0.05%, the treatment of blanched raw peanut kernels resulted in higher concentrations of Ara h1 and Ara h2. When the concentration of α-chymotrypsin increased to 0.10%, the concentration of Ara h1 decreased, but the concentration of Ara h2 increased. Significant reduction in the concentration of Ara h2 was achieved only when the concentration of α-chymotrypsin increased to about 0.15% and with longer incubation time.

TABLE 5

Allergen change in blanched roasted peanut kernels after α-chymotrypsin treatment

| Enzyme Concentration | Time hr | Protein (mg/ml) | Ara h1 (mg/g protein) | Ara h2 (mg/g protein) | % Ara h1 change | % Ara h2 change |
|---|---|---|---|---|---|---|
| 0.01% | 1 | 2.58 | 0.41 ± 0.01 | 0.28 ± 0.09 | −90 | −81 |
|       | 3 | 2.79 | 0.57 ± 0.08 | 0.26 ± 0.05 | −86 | −83 |
|       | 5 | 2.74 | 1.23 ± 0.15 | 0.30 ± 0.06 | −68.75 | −79.83 |
| 0.05% | 1 | 3.96 | 0.25 ± 0.06 | 0.05 ± 0.04 | −94 | −98 |
|       | 3 | 4.20 | 0.08 ± 0.06 | 0.03 ± 0.02 | −98 | −98 |
|       | 5 | 3.86 | 0.09 ± 0.04 | 0.01 ± 0.01 | −98 | −100 |

TABLE 5-continued

Allergen change in blanched roasted peanut kernels after α-chymotrypsin treatment

| Enzyme Concentration | Time hr | Protein (mg/ml) | Ara h1 (mg/g protein) | Ara h2 (mg/g protein) | % Ara h1 change | % Ara h2 change |
|---|---|---|---|---|---|---|
| 0.10% | 1 | 4.14 | 0.07 ± 0.04 | 0.00 ± 0.00 | −98 | −100 |
|  | 3 | 4.12 | 0.02 ± 0.03 | 0.00 ± 0.02 | −100 | −100 |
|  | 5 | 4.03 | 0.00 ± 0.00 | 0.00 ± 0.00 | −100 | −100 |
| 0.15% | 1 | 4.91 | 0.00 ± 0.00 | 0.00 ± 0.00 | −100.00 | −100.00 |
|  | 3 | 4.56 | 0.00 ± 0.00 | 0.00 ± 0.00 | −100.00 | −100.00 |
|  | 5 | 4.85 | 0.00 ± 0.00 | 0.00 ± 0.00 | −100.00 | −100.00 |

Table 5 shows that prior blanching of light-roasted peanut kernels significantly enhanced the effectiveness of α-chymotrypsin in inactivating Ara h1 and Ara h2. Data show that, regardless of time, higher enzyme concentrations yielded higher reduction in Ara h1 and Ara h2 concentrations, and thus lower allergenic activity. Specifically, at a concentration of α-chymotrypsin of about 0.15%, all Ara h1 and Ara h2 were eliminated from roasted peanut kernels, regardless of treatment time. Thus, shorter treatment time of less than 1 hour can be used to completely inactivate peanut allergens at enzyme concentrations as low as about 0.15%.

Example 2

Enzyme Treatments

Samples of both raw and roasted peanut kernels (purchased from Good Earth Peanut Co., Skippers, Va.) were weighed in 25 g portions and placed in separate 250 ml flasks. These kernel samples were then blanched in boiling water for about 5 minutes. They were then drained and cooled to room temperature. Afterwards, each 25 g kernel sample was transferred to its own individual flask. Fifty milliliters of a control solution, consisting of distilled water was prepared. Fifty milliliters of enzyme solution containing 0.001, 0.01, 0.1, 0.2, 0.3, 0.4, and 0.5% of α-chymotrypsin (purchased from Sigma-Aldrich, St. Louis, Mo.) were added to individual flasks containing 25 g blanched and drained peanut kernels. The flasks containing the peanut kernels and enzyme solutions were capped and incubated at about 37° C. for about 3 hours. After incubation, the kernel samples were dried at about 65-70° C. in a preheated vacuum oven overnight to remove excess water and to inactivate the enzymes. The dried kernels were then ground into flour using a high-speed blender. Dried flour samples were labeled and stored at about 4° C. until used.

Treatment of roasted peanut kernels with trypsin was done the same way as α-chymotrypsin treatment, but the enzyme concentrations tested were 0.001, 0.005, 0.01, 0.05, and 0.1% (w/w). However, treatment of peanut kernels with pepsin was conducted at a pH of about 3.0 using a citric buffer, because pepsin would lose its activity at a pH of about 6.0 or higher. Pepsin concentrations tested were 0.001, 0.002, 0.004, 0.005, 0.01, 0.05, and 0.1%. Trypsin and pepsin were both purchased from Sigma-Aldrich of St. Louis, Mo.

Extraction of peanut protein: One gram of peanut flour from each sample was mixed with 20 ml of Tris-HCl buffer (pH 8.3) and stirred at room temperature for about 2 hours. Mixtures were then centrifuged at about 3000 g for about 20 minutes. The lipid layer on the top of the supernatant was removed using transfer pipettes. Excess supernatant was stored at about −20° C. for further analysis.

Determination of soluble protein in extracts: The amount of soluble protein in each lipid extract was determined by the bicinchoninic acid (BCA) method using bovine serum albumin (BSA) as the standard. The peanut protein extracts were diluted about 5-10 times with deionized water to bring the protein concentration of the test samples within the linear range of the BSA calibration curve (0-1.0 mg/ml).

Determination of Ara h1 and Ara h2: A direct Enzyme-Linked Immunosorbent Assay (ELISA) method was used to determine Ara h1 and Ara h2 in peanut extracts from treated and untreated peanut kernels, using chicken anti-Ara h1 and anti-Ara h2 as primary antibodies, and peroxidase labeled anti-chicken antibody as the detection antibody. In order to make the spectrometric detection of the allergens Ara h1 and Ara h2, 2,2'-azino-bis(3-ethylbenzthiazoline-6-sulphonic acid) (ABTS) was used as the enzyme substrate. Purified Ara h1 and Ara h2 (provided by Dr. Melaki, USDA-ARS) were used as positive controls and in developing standard curves used in quantitation. Final results were calculated as mg Ara h1/g soluble protein or mg Ara h2/g soluble protein.

SDS-PAGE: Depending on the protein concentration of each peanut extract, as determined by the BCA method, extracts were diluted quantitatively to a protein concentration of about 1.0 mg/ml with SDS-PAGE buffer, then boiled at about 90° C. for about 10 minutes to completely denature the proteins. After cooling to room temperature, samples were loaded on a polyacrylamide gel (10 μl/well). Following staining, bands were identified using molecular weight markers and purified Ara h1 and Ara h2.

Results: Table 6 shows that the soluble protein of the peanut kernels treated with α-chymotrypsin increased as compared to the untreated kernels. The protein soluble concentrations of all extracts from the α-chymotrypsin-treated peanut kernels reveals that soluble protein levels actually increased with increasing enzyme concentration. Even the lowest enzyme concentration used (0.001%) showed a slight increase in the soluble protein over the untreated control. This demonstrated that the treatment of the peanut kernels with α-chymotrypsin was effective in increasing the protein solubility of the peanut kernels, probably through proteolytic breakdown into smaller more soluble proteins. Similar results were observed for trypsin (Table 6).

TABLE 6

Effect of enzyme type and concentration on reduction of Ara h1 and Ara h2 in roasted peanut kernels (incubation time about 3 hours at about 37° C.)

| Enzyme type | Enzyme (%) | Soluble protein (mg/ml) | Ara h1 (mg/g) protein | % Ara reduction | Ara h2 (mg/g) protein | % Ara reduction |
|---|---|---|---|---|---|---|
| Control (untreated) | 0 | 2.31 | 8.28 | — | 1.95 | — |
| α-chymotrypsin | 0.5 | 5.41 | 0.00 | 100.00 | 0 | 100 |
|  | 0.4 | 5.49 | 0.05 | 95.76 | 0.1 | 96 |
|  | 0.3 | 4.58 | 0.00 | 100.00 | 0 | 100 |

TABLE 6-continued

Effect of enzyme type and concentration on reduction of Ara h1 and Ara h2 in roasted peanut kernels (incubation time about 3 hours at about 37° C.)

| Enzyme type | Enzyme (%) | Soluble protein (mg/ml) | Ara h1 (mg/g) protein | % Ara h1 reduction | Ara h2 (mg/g) protein | % Ara h2 reduction |
|---|---|---|---|---|---|---|
|  | 0.2 | 4.71 | 0.05 | 97.77 | 0 | 98 |
|  | 0.1 | 4.29 | 0.23 | 97.19 | 0.2 | 92 |
|  | 0.01 | 3.16 | 1.00 | 87.92 | 0.4 | 78 |
|  | 0.001 | 2.39 | 2.63 | 68.26 | 1 | 50 |
| trypsin | 0.5 | 5.74 | 0.00 | 99.28 | 0 | 100 |
|  | 0.4 | 5.58 | 0.00 | 100.00 | 0 | 100 |
|  | 0.3 | 5.50 | 0.00 | 100.00 | 0 | 100 |
|  | 0.2 | 3.92 | 0.00 | 100.00 | 0 | 100 |
|  | 0.1 | 6.55 | 0.00 | 100.00 | 0 | 100 |
|  | 0.01 | 4.34 | 0.34 | 95.88 | 0.3 | 86 |
|  | 0.001 | 2.13 | 2.92 | 64.69 | 1 | 57 |

Table 6 shows the effect of enzyme type and enzyme concentration on the reduction of Ara h1 and Ara h2 in roasted peanut kernels at a treatment time of about 3 hours and an incubation temperature of about 37° C. It was observed that the use of solutions containing about 0.2% (w/w) and higher α-chymotrypsin resulted in the complete inactivation of both Ara h1 and Ara h2. It was also observed that the use of solutions containing about 0.1% (w/w) and higher trypsin resulted in the complete inactivation of both Ara h1 and Ara h2. It was further observed that the level of Ara h1 and Ara h2 inactivation increased linearly with enzyme concentration, but reached a maximum at enzyme concentrations between about 0.1% and about 0.2% (w/w), after which allergen inactivation leveled off and remained constant at about 100%. However, this maximum activity will depend on the experimental conditions used to treat the peanuts, and this maximum may shift upward or downward.

TABLE 7

Effects of enzyme treatment time on the reduction of Ara h1 and Ara h2 in roasted peanut kernels at a total enzyme concentration of about 0.15% (w/w) and incubation temperature of about 37° C.

| Enzyme type | Enzyme time (hr) | Soluble protein (mg/ml) | Ara h1 (mg/g) | % Ara h1 reduction | Ara h2 (mg/g) | % Ara h2 reduction |
|---|---|---|---|---|---|---|
| Control | 0 | 2.69 | 6.87 | — | 1.27 | — |
| α-chymotrypsin | 0.25 | 6.53 | 0.00 | 100.00 | 0 | 100 |
|  | 0.5 | 6.23 | 0.03 | 99.52 | 0 | 100 |
|  | 1.0 | 5.96 | 0.00 | 100.00 | 0 | 100 |
|  | 2.0 | 6.54 | 0.00 | 100.00 | 0 | 100 |
|  | 3.0 | 6.43 | 0.00 | 100.00 | 0 | 100 |
|  | 4.0 | 6.65 | 0.00 | 100.00 | 0 | 100 |
|  | 5.0 | 6.27 | 0.00 | 100.00 | 0 | 100 |
|  | 6.0 | 6.80 | 0.00 | 100.00 | 0 | 100 |
|  | 7.0 | 6.23 | 0.00 | 100.00 | 0 | 100 |
|  | 8.0 | 5.78 | 0.00 | 100.00 | 0 | 100 |
| trypsin | 0.25 | 7.28 | 0.00 | 100.00 | 0 | 98 |
|  | 0.5 | 7.28 | 0.00 | 100.00 | 0 | 100 |
|  | 1.0 | 7.33 | 0.00 | 100.00 | 0 | 100 |
|  | 2.0 | 7.37 | 0.00 | 100.00 | 0 | 100 |
|  | 3.0 | 7.31 | 0.00 | 100.00 | 0 | 99 |
|  | 4.0 | 7.14 | 0.00 | 100.00 | 0 | 98 |
|  | 5.0 | 7.22 | 0.00 | 100.00 | 0 | 100 |
|  | 6.0 | 6.85 | 0.00 | 100.00 | 0 | 98 |
|  | 7.0 | 6.98 | 0.00 | 100.00 | 0 | 99 |
|  | 8.0 | 7.46 | 0.00 | 100.00 | 0 | 96 |

Table 7 shows the effects of enzyme treatment time on the reduction of Ara h1 and Ara h2 in roasted peanut kernels at a total enzyme concentration of about 0.15% (w/w) and an incubation temperature of about 37° C. Two 0.15% (w/w) enzyme solutions were utilized: a solution containing α-chymotrypsin alone, and a solution containing trypsin alone. Total treatment time with each of the two enzyme solutions was 8 hours, with measurements of soluble protein (mg/ml), Ara h1 (mg/g) and Ara h2 (mg/g) taken at intervals of 15 minutes, 30 minutes, 1 hour, and hourly thereafter up to and including 8 hours. It was observed that the enzyme action on Ara h1 and Ara h2 was extremely fast, resulting in the near elimination of these two allergens within about 15 minutes (0.25 hrs). The efficiency of the enzymatic reaction continued to increase with time for up to about one hour, after which enzyme activity remained constant or leveled off slightly.

While the present invention has been described in connection with the above-identified embodiments, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

What is claimed is:

1. A method for reducing the allergenic protein content of a peanut kernel, comprising blanching a roasted peanut kernel then contacting said blanched, roasted peanut kernel with a hypoallergenically-effective amount of at least one endopeptidase enzyme,
    wherein said hypoallergenically-effective amount is from about 0.001% to about 0.5% (w/w); and
    wherein said roasted peanut kernel is incubated with said endopeptidase enzyme for about 0.25 hours to about 8 hours.

2. The method according to claim 1 wherein said endopeptidase enzyme is any one of pepsin, trypsin, or α-chymotrypsin.

3. The method according to claim 2 wherein said endopeptidase enzyme is pepsin.

4. The method according to claim 2 wherein said hypoallergenically-effective amount is from about 0.1% to about 0.2% (w/w).

5. The method according to claim 2 wherein said endopeptidase enzyme is trypsin or α-chymotrypsin.

6. A hypoallergenic peanut product produced according to the method of claim 1.

7. A peanut-containing food product wherein the allergenicity of said peanut-containing food product has been reduced by greater than about 30% by the method according to claim 1.

8. The method according to claim 1 wherein said roasted peanut kernel is incubated with said endopeptidase enzyme at a pH from about 6 to about 11 and said endopeptidase enzyme is trypsin or α-chymotrypsin.

9. The method according to claim 1 wherein said roasted peanut kernel is incubated with pepsin at a pH from about 1 to about 3.

10. The method of claim 1 wherein said allergenic protein content is reduced by greater than about 30%.

11. The method of claim 10 wherein said allergenic protein content is reduced by about 100%.

* * * * *